United States Patent [19]
Reichert et al.

[11] Patent Number: 5,616,555
[45] Date of Patent: Apr. 1, 1997

[54] CRYSTALLINE R-H-GM-CSF AND METHOD

[75] Inventors: Paul Reichert, Montville; Gerald S. Hammond, Montclair; Hung V. Le, Rockaway; Tattanahalli L. Nagabhushan, Parsippany; Paul P. Trotta, Rutherford, all of N.J.

[73] Assignee: Schering Corporation, Kenilworth, N.J.

[21] Appl. No.: 482,168

[22] Filed: Jun. 7, 1995

Related U.S. Application Data

[63] Continuation of Ser. No. 337,578, Nov. 10, 1994, abandoned, which is a continuation of Ser. No. 806,408, Dec. 13, 1991, abandoned, which is a division of Ser. No. 362,187, Jun. 6, 1989, Pat. No. 5,109,119.

[51] Int. Cl.$^6$ .............................. A61K 38/16; C07K 1/00; C07K 14/00; C07K 17/00
[52] U.S. Cl. ................... 514/8; 514/12; 530/350; 530/351; 424/85.1; 435/69.5
[58] Field of Search ..................... 530/350, 351; 424/85.1; 435/69.5; 514/8, 12

[56] References Cited

U.S. PATENT DOCUMENTS 4,912,200  3/1990  Leibowitz et al. ................ 530/351

OTHER PUBLICATIONS

Baldwin et al., Proc. Natl. Acad. Sci. USA 85:2763 (1988).
Brandt et al., New Eng. J. Med 318:869 (1988).
Burgess et al., Blood 69:43 (1987).
Cantrell et al., Proc. Natl. Acad. Sci. USA 82:6250 (1985).
Clark et al., Science 236:1229 (1987).
Donahue et al., Nature 321:872 (1986).
Gasson et al., Science 226:1339 (1984).
Greenberg et al., Curr. Microbiol. 17:321 (1988).
Groopman et al., New Eng. J. Med. 317:593 (1987).
Kaushansky et al., Proc. Natl. Acad. Sci. USA 83:3101 (1985).
La Londe et al., J. Mol. Biol. 205:783 (1989).
Mayer et al., Blood 70:206 (1987).
McPherson, J. Biol. Chem. 251:6300 (1976).
Metcalf, Science 229:16 (1985).
Metcalf, Blood 67:257 (1986).
Morstyn et al., Cancer Res. 48:5624 (1988).
Schrimsher et al., Biochem. J. 247:195 (1987).
Scopes, Protein Purification, Principles and Practices, 1988, Springer–Verlag, New York, pp. 296–301 and 320–321.
Tomonaga et al., Blood 67:31 (1986).
Vadhan–Raj et al., New Eng. J. Med. 317: 1545 (1987).
Ward et al., J. Mol. Biol. 98:161 (1975).
Wingfield et al., Eur. J. Biochem. 173:65 (1988).

*Primary Examiner*—Frederick Krass
*Attorney, Agent, or Firm*—Paul G. Lunn; Norman C. Dulak

[57] ABSTRACT

This invention provides a crystalline form of recombinant human granulocyte-macrophage colony-stimulating factor (r-h-GM-CSF) and methods for making such crystals.

13 Claims, No Drawings

CRYSTALLINE R-H-GM-CSF AND METHOD

The present application is a continuation of U.S. application Ser. No. 08/337,578 filed Nov. 10, 1994, now abandoned which was a continuation of U.S. application Ser. No. 07/806,408, filed Dec. 13, 1991, now abandoned which is a divisional of U.S. application Ser. No. 07/362,187 filed Jun. 6, 1989 issued as U.S. Pat. No. 5,109,119.

This invention relates to recombinant human granulocyte-macrophage colony-stimulating factor (r-h-GM-CSF), and in particular to a crystalline form thereof.

Colony-stimulating factors represent a family of proteins that are required in vitro for the survival, proliferation and differentiation of hematopoietic progenitor cells of myeloid and erythroid lineage: Metcalf, D., *The Hemopoietic Colony Stimulating Factors,* Elsevier, Amsterdam (1984); Metcalf, D., *Science,* 229, 16–22 (1985); Metcalf, D., *Blood* 67, 257–267 (1986); and Clark, S. C., et al., *Science* 236, 1229–1237 (1987). Granulocyte-macrophage colony-stimulating factor (GM-CSF) stimulates the production of colonies of granulocytes and macrophages from their precursor cells and also promotes the growth and differentiation of pluripotent progenitor cells. In addition, GM-CSF can enhance a variety of the functional activities of mature effector cells [as reviewed by Morstyn, G., et al., *Cancer Res.* 48, 5624–5637 (1988)] and promote the differentiation of myeloid leukemic cells [Tomonaga, M., et al., *Blood* 67, 31–36 (1986)]. Although human GM-CSF has been purified from natural sources [Gasson, J. C., et al., *Science* 226, 1339–1342 (1984)], the low quantities produced have not permitted detailed characterization of its physiochemical and biological properties. The cloning of the complementary DNA encoding human GM-CSF and its expression in bacterial and mammalian cell hosts has enabled the preparation of large quantities of purified recombinant protein [Greenberg, R., et al., *Curr. Micro.,* 17, 321–332 (1988); Burgess, A. W., et al., *Blood* 69, 43–51 (1987); and Lee, F., et al., *Proc. Natl. Acad. Sci (USA)* 83, 3101–3105 (1985)]. Based on in vitro biology and the activity of GM-CSF in animal models [Mayer, P., et al., *Blood* 70, 206–213 (1987), and Donahue, R. E., et al., *Nature* 321, 872–875 (1986)], phase I/II clinical trials on recombinant GM-CSF have been initiated in myelodysplastic syndromes [Vadhan-Raj, S., et al., *N Engl. J. Med.* 317, 1545–1551 (1987)], acquired immunodeficiency syndrome [Groopman, J. E., et al., *N. Engl. J. Med.* 317, 593–598 (1987), and Baldwin G. C., et al., *Proc. Natl. Acad. Sci. (USA)* 85, 2763–2766 (1988)], and cancer [Brandt, S. J., et al., *N. Engl. J. Med.* 318, 869–876 (1988)].

The mature protein sequence of human GM-CSF consists of 127 amino acids, including four cysteine residues that form two disulfide linkages [Lee, F., et al., *Proc. Natl. Acad. Sci. (USA)* 83, 3101–3105 (1985), Cantrell, M. A., et al., *Proc. Natl. Acad. Sci. (USA)* 82, 6250–6254 (1985), and Schrimsher, J. L. et al., *Biochem. J.* 247, 195–199 (1987)]. Physical studies have suggested that human GM-CSF is a compact globular protein containing both alpha helical and beta sheet structures [Wingfield, P., et al., *Eur. J. Biochem,* 173, 65–72 (1988)].

We have now obtained crystalline, human, recombinant GM-CSF. The crystalline GM-CSF of the invention preferably is mature, human, recombinant GM-CSF lacking an N-terminal methionine and having a methionine at position 80. We have demonstrated that the crystalline r-h-GM-CSF retains its full activity, i.e., upon redissolution in an aqueous system it possesses essentially the same activity as the r-h-GM-CSF starting material used in preparing the crystals. We have also characterized the crystals by X-ray crystallographic analysis. Preferably, the crystalline GM-CSF is non-glycosylated and is derived from E. coli. In a preferred embodiment, the r-h-GM-CSF used in the present invention, has the following complete amino acid sequence:

(H) Ala Pro Ala Arg Ser Pro Ser Pro Ser Thr(10)
Gln Pro Trp Glu His Val Asn Ala Ile Gln(20) Glu Ala
Arg Arg Leu Leu Asn Leu Ser Arg(30) Asp Thr Ala
Ala Glu Met Asn Glu Thr Val(40) Glu Val Ile Ser Glu
Met Phe Asp Leu Gln(50) Glu Pro Thr Cys Leu Gln
Thr Arg Leu Glu Glu(60) Leu Tyr Lys Gln Gly Leu Arg
Gly Ser Leu(70) Thr Lys Leu Lys Gly Pro Leu Thr
Met Met(80) Ala Ser His Tyr Lys Gln His Cys Pro
Pro(90) Thr Pro Glu Thr Ser Cys Ala Thr Gln
Ile(100) Ile Thr Phe Glu Ser Phe Lys Glu Asn
Leu(110) Lys Asp Phe Leu Leu Val Ile Pro Phe
Asp(120) Cys Trp Glu Pro Val Gln Glu (OH).

The present invention also involves a method for making GM-CSF crystals in which a solution of GM-CSF, especially r-h-GM-CSF, is equilibrated against a second solution that will cause the GM-CSF solution to become more concentrated and form GM-CSF crystals. Preferably, the equilibration occurs slowly, e.g., over 5 to 30 days. The concentration of GM-CSF in its solution is preferably at least 20 mg/ml, more preferably from 40 to 250 mg/ml.

The method of this invention is not limited to use with r-h-GM-CSF or the GM-CSF having the amino acid sequence described above. The method may be used with various forms of GM-CSF (for example, glycosylated or non-glycosylated GM-CSF, irrespective of the mammalian species to which it pertains and whether or not it contains a leader sequence). Mutant and allelic forms of GM-CSF may also be used. Preferably, the glycosylated forms of GM-CSF will be chromatographed to attain constant molecular weight prior to crystallization. Most preferably, however, the GM-CSF used in the method of the invention is derived from E. coli and is mature, human, recombinant GM-CSF lacking an N-terminal methionine and having a methionine at position 80, e.g., the r-h-GM-CSF having the complete amino acid sequence described above.

Suitable methods of equilibration include dialysis, ultrafiltration, e.g. diafiltration, or using drops, e.g., hanging or sandwiched droplets. Equilibration can be effected with a second solution of a suitable solute that is more concentrated than the solution of GM-CSF. A particularly preferred method is to equilibrate a solution of r-h-GM-CSF against a polyethylene glycol solution, which PEG preferably has a molecular weight of at least 1,000, e.g. 4,000 to 40,000.

In a preferred embodiment, a pure solution of GM-CSF in a suitable buffer, e.g., at pH 6.5 to 8.5, especially sodium phosphate at pH 7.0 to 8.0, and in polyethylene glycol (PEG), e.g., PEG-8000, is allowed to equilibrate against a more concentrated solution of PEG, preferably the same PEG. The concentration of the buffer can range widely, e.g. from 1 mM to 1,000 mM, preferably from 10 to 400 mM, especially 16 to 320 mM. After several days' equilibration at a suitable temperature, e.g., from just above the freezing temperature of the solution up to 20° C., preferably 0°–°10° C., crystals will usually have formed. Such crystals can then be used as seed crystals for further batches of GM-CSF crystals.

EXPERIMENTAL PROCEDURES

Human GM-CSF was expressed periplasmically in *E. coli* with a secretory vector, pINIIIompA2 [Greenberg, R., et al., *Curr. Micro.,.* 17, 321–332 ( 1988)]. Other methods for the expression of r-h-GM-CSF can be used; for example that of Lee et al., *Proc. Natl. Acad. Sci, (USA)* 82, 4060–4064 (1985). It was purified by conventional chromatography, as previously described (International Patent Application no. PCT/US 88/02294, Schering Corporation and Trotta, P. P., et al., published 26th Jan. 1989 as WO 89/00579, corresponding to U.S. application Ser. No. 074,410 filed Jul. 16, 1987), followed by reversed-phase high-performance liquid chromatography (HPLC) on a Rainin Dynamax-300Å C-4 column using a 27–72% gradient of acetonitrile in 0.1% trifluoroacetic acid.

Crystals suitable for X-ray analysis were obtained by vapor-diffusion equilibration using either hanging droplets or sandwiched droplets. For hanging droplets, 20 µl droplets containing 20 mg/ml of protein in 10% polyethylene glycol 8000 (PEG-8000), 16 mM sodium phosphate, pH 8.0, were hung from siliconized coverslips inverted on Linbro plates. These droplets were equilibrated against 1 ml of 20% PEG-8000 in 16 mM sodium phosphate, pH 8.0. After 10–15 days at 4° C., orthorhombic crystals with dimensions up to 2.0 mm×0.60 mm×0.10 mm were obtained. Alternatively, for sandwiched droplet vapor-diffusion experiments, 20 µl droplets containing 20 mg/ml of protein in 10% PEG-8000, 16 mM sodium phosphate, pH 8.0, were equilibrated against 1 ml of 20% PEG-8000 in 16 mM sodium phosphate, pH 8.0. After 15–20 days at 4° C., crystals of the same general morphology and size appeared. In each procedure the crystals grew within the pH range of 6.5 to 8.5, preferably 7.0–8.0; we have obtained the best crystals at pH 8.0.

For X-ray studies, crystals were mounted in glass capillaries and were photographed with a precession camera at 22° C. using CuKα radiation from a Rigaku RU-300 rotating anode generator operating at 40 kV and 100 mA. A complete native data set was collected on a Nicolet X-100A area detector using the same radiation source.

Several batches of crystals, some prepared by the hanging droplet method and some by the sandwiched droplet method, were subjected to X-ray analysis and gave consistent results as to space group and unit cell size. The results are described below.

The crystalline GM-CSF of the invention can be used in basically the same manner in which prior GM-CSF materials have been used in pharmaceutical preparations, e.g., depot preparations of GM-CSF, which can be designed to administer a daily dose of 0.1 µg/kg to 100 µg/kg of GM-CSF. Such preparations contain a physiologically effective amount of the crystalline GM-CSF in association with a conventional pharmaceutically acceptable carrier.

CHARACTERIZATION

1. BIOASSAY

Individual crystals were extracted from hanging droplets with a syringe, and then resuspended in 100 µl of wash solution consisting of 20% PEG 8,000, 16 mM sodium phosphate, pH 7.5 at 4° C. The suspension was centrifuged and the wash solution was removed with a Pasteur pipette. The washed crystals were redissolved in 100 µl of 20 mM sodium phosphate, pH 7.5, 0.15M sodium chloride, at 25° C.

A protein determination and a cell-proliferation assay [Mosmann, T. J., *Journal of Immuno. Methods* 65, 55–63 (1983)] using the KG-1 cell line on the redissolved crystal solution yielded a specific activity of $2.7 \times 10^8$ units/mg. This value is the same as that obtained for the original GM-CSF preparation prior to crystallization, within the limits of the precision of the assay (typically within the range $2 \times 10^8$ to $3 \times 10^8$ units per mg).

2. HPLC

Analytical high performance reversed-phase liquid chromatography was run on an aliquot of the redissolved-crystal solution on a Rainin Dynamax C8 widepore (4.6 mm×25 cm) column using a 27% acetonitrile: 0.1% trifluoroacetic acid to 72% acetonitrile: 0.1% trifluoroacetic acid linear gradient over a 30 minute period on a Waters analytical HPLC system. A Gilson variable wavelength detector set at 280 nm with a sensitivity of 0.02 absorbance units was used to monitor peaks. The retention times and chromatographic profiles of both the redissolved-crystal solution and the original GM-CSF preparation prior to crystallization were identical.

From 1. and 2. above, there is clearly no reason to suppose that any chemical changes or any denaturing of the protein took place during the crystallization or reconstitution.

3. X-RAY DIFFRACTION ANALYSIS

X-ray diffraction data were initially collected to 2.8Å resolution using the area detector. Oscillation frames covered 0.25° and were measured for 10 min. A total of 6,797 reflections were measured; these were merged into 3,841 unique reflections. Indexing and integration of intensity data were carried out using XENGEN processing programs [Howard, A. J., et al., *J. Appl. Crystallogr.* 20, 383–387 (1987)]. The $R_{sym}$ value (based on I) for the data to 3.0Å was 0.087. The data indexed in the orthorhombic system with a=126.9±2Å, b=47.4±1Å and c=59.1±1Å. The space group $P2_12_12_1$ was specified by the systematic absence of reflections h00 with h=2n+1, 0k0 with k=2n+1, and 00l with l=2n+1. Subsequent X-ray precession photographs of GM-CSF confirmed the space group and the unit cell dimensions. The crystals are stable to X-rays at room temperature for at least three days and diffract to 2.5Å resolution or better.

Based on a molecular weight of 14,477 daltons as predicted from the cDNA of the crystalline r-h-GM-CSF used [Lee, F., et al., *Proc. Natl. Acad. Sci. (USA)* 83, 3101–3105 (1985)], the calculated values of $V_m$ [Matthews, B. W., *J. Mol. Biol.* 33, 491–497 (1968)] for two or three molecules per crystallographic asymmetric unit are 3.07 and 2.05, respectively. Assuming a partial specific volume of 0.724 cm³/g [Wingfield, P., et at.,*Eur. J. Biochem.* 173, 65–72 (1988)], these values correspond to solvent volume fractions of 59% and 39%, respectively. The corresponding $V_m$ values for one and four molecules per crystallographic asymmetric unit are 6.14 and 1.53, respectively, which are far outside the limits normally observed for proteins. Therefore, it appears that the protein crystallizes with either two or three molecules in the asymmetric unit. A self-rotation function that was calculated using the native data collected on the area detector did not show a noncrystallographic 2-fold or 3-fold axis.

We claim:

1. Crystalline, mature human recombinant non-glycosylated Granulocyte Macrophage-Colony Stimulating Factor (GM-CSF).

2. Crystalline GM-CSF as claimed in claim 1 having the amino acid sequence:

---

(H) Ala Pro Ala Arg Ser Pro Ser Pro Ser Thr Gln Pro
Trp Glu His Val Asn Ala Ile Gln Glu Ala Arg Arg Leu
Leu Asn Leu Ser Arg Asp Thr Ala Ala Glu Met Asn
Glu Thr Val Glu Val Ile Ser Glu Met Phe Asp Leu Gln
Glu Pro Thr Cys Leu Gln Thr Arg Leu Glu Leu Tyr
Lys Gln Gly Leu Arg Gly Ser Leu Thr Lys Leu Lys Gly
Pro Leu Thr Met Met Ala Ser His Tyr Lys Gln His
Cys Pro Pro Thr Pro Glu Thr Ser Cys Ala Thr Gln Ile
Ile Thr Phe Glu Ser Phe Lys Glu Asn Leu Lys Asp

Phe Leu Leu Val Ile Pro Phe Asp Cys Trp Glu Pro
Val Gln Glu (OH).

3. Crystalline GM-CSF as claimed in claim 1 which, when redissolved, retains substantially its full biological activity.

4. A pharmaceutical composition which comprises crystalline mature, nonglycosylated, human recombinant GM-CSF in association with a pharmaceutically acceptable carrier.

5. A pharmaceutical composition as claimed in claim 4 wherein the GM-CSF is crystalline, mature, human recombinant GM-CSF lacking N-terminal methionine and having Met80.

6. A pharmaceutical composition as claimed in claim 4 wherein the composition is a depot formulation.

7. Crystalline mature human, nonglycosylated GM-CSF wherein said crystalline GM-CSF diffracts x-rays to $\geq 2.5\text{Å}$.

8. Crystalline GM-CSF of claim 7 having an $R_{sym}$ value of 0.087 for x-ray diffraction data collected to a resolution of 3.0Å.

9. Crystalline mature human non-glycosylated GM-CSF wherein said crystalline GM-CSF is orthorhombic.

10. Crystalline GM-CSF of claim 9 wherein the crystalline GM-CSF has space group $P2_12_12_1$.

11. The crystalline GM-CSF of claim 9 wherein the crystalline GM-CSF has unit cell dimensions $a=1.26.9\pm 2\text{Å}$, $b=47.4\pm 1\text{Å}$, and $c=59.1\pm 1\text{Å}$.

12. Crystalline mature, nonglycosylated human GM-CSF having either two or three molecules in an asymmetric unit.

13. Crystalline mature, nonglycosylated human GM-CSF having a ratio of unit cell volume to protein molecular mass in a unit cell volume (Vm) of 3.07 and 2.05 for two or three molecules respectively per crystallographic asymmetric unit.

* * * * *